United States Patent [19]

Hamashima et al.

[11] Patent Number: 4,647,658

[45] Date of Patent: Mar. 3, 1987

[54] PROCESS FOR PREPARING AMINOHYDROXYCEPHAMCARBOXYLATES

[75] Inventors: Yoshio Hamashima, Kyoto; Fumitaka Takami, Nara, both of Japan

[73] Assignee: Shionogi & Co., Ltd., Osaka, Japan

[21] Appl. No.: 739,302

[22] Filed: May 29, 1985

[30] Foreign Application Priority Data

Jun. 8, 1984 [JP] Japan ............................... 59-118698
Dec. 28, 1984 [JP] Japan ............................... 59-275709

[51] Int. Cl.$^4$ .......................................... C07D 501/20
[52] U.S. Cl. .................................... 540/215; 540/222
[58] Field of Search ................. 544/16, 22; 540/215, 540/214, 222

[56] References Cited

U.S. PATENT DOCUMENTS 3,989,695 11/1976 Scartazzini ............................ 544/22

FOREIGN PATENT DOCUMENTS 0016725 10/1980 European Pat. Off. ............. 544/16

*Primary Examiner*—Sam Rosen
*Assistant Examiner*—Robert Benson
*Attorney, Agent, or Firm*—Wenderoth, Lind & Ponack

[57] ABSTRACT

A useful synthetic intermediate, 7-amino-3-acyloxycepham-4-carboxylic acid aralkyl ester, is prepared by reducing 7-amido-3-oxocepham-4-carboxylic acid aralkyl ester with alkali metal borohydride in a dry organic solvent at temperature lower than −20° C. and then acylating the resulting 3-hydroxycepham compound with an acylating reagent to give 3-acyloxycepham compound, and then subjecting the 3-acyloxycepham compound to amide cleavage consisting of treatments (1) with a mixture of phosphorus pentachloride and aromatic base giving imino-chloride and (2) with alcohol for converting the latter into imino-ether and for subjecting the product to alcoholysis giving the objective compound.

6 Claims, No Drawings

PROCESS FOR PREPARING AMINOHYDROXYCEPHAMCARBOXYLATES

This invention relates to (1) a reduction of 3-oxocepham compound to give 3-hydroxycephem compound at low temperature and (2) an amide cleavage of 7-amido-3-acyloxycephem compound to give new 7-amino-3-acyloxycepham compound with an aromatic base in place of tertiary amine in a known analogous amide cleavage.

The cepham or cephem compounds in this invention have a 7-amido group and a 4-carboxylic acid aralkyl ester group.

The 7-amido group is acylamido known in penicillin or cephalosporin field and is stable under the condition of this invention. For example, representative acyls available in the 7-amido group are shown by the following formula:

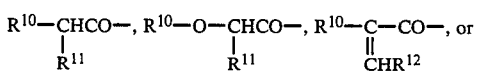

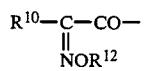

{wherein
R$^{10}$ is phenyl or 5 membered monocyclic hetero aromatic group (e.g., phenyl, thienyl, thiazolyl, thiadiazolyl) substituted by R$^{11}$;

R$^{11}$ has up to 8 carbon atoms and can be hydrogen, protected carboxy, alkylureido, alkoxycarbonylamino, aralkoxycarbonylamino, hydroxy, or halogen; and R$^{12}$ is halogen, alkyl-R$^{11}$, O-alkyl-R$^{11}$, or S-alkyl-R$^{11}$ (in which alkyl has up to 5 carbon atoms)}.

The aralkyl group in the 4-carboxylic acid aralkyl ester group has 7 to 15 carbon atoms and is easily cleavable (e.g., benzyl, methoxybenzyl, diphenylmethyl esters).

REDUCTION

The first aspect of this invention is an improved process for preparing 3-hydroxycepham-4-carboxylic acid aralkyl esters by reducing the corresponding 3-oxocepham-4-carboxylic acid aralkyl ester or its enolate with alkali metal borohydride in a dry inert organic solvent at temperature lower than −20° C.

This reaction itself is known from Japanese Patent Application (kokai) Sho 49-49989. However, the present inventors found that the reduction of an aralkyl ester under the known aqueous condition caused a cleavage of ester moiety giving a lot of aralkyl alkohol and resulted a lower yield of the desired ester. Then they tried to cool the reaction medium beyond the disclosed range of the said patent publication to about −50° C. in an ahydrous organic solvent to find that the reduction proceeded in high yield without side reaction as shown in Table 1. Based on this observation they have completed this invention.

TABLE 1

| Temperature dependence of NaBH$_4$ reduction | |
|---|---|
| Temperature | Yield |
| 0 | 15% |
| −10 | 30 |
| −30 | 65 |
| −50 | 84 |
| −70 | 96 |

| Reaction condition | |
|---|---|
| NaBH$_4$ | 2 equiv. |
| CH$_2$Cl$_2$ | 7 parts |
| MeOH | up to 4 parts |
| time | 30 minutes. |

The said inert organic solvent is preferably a substantially anhydrous polar organic solvent, for example, lower alkanol (e.g., methanol, ethanol, propanol, butanol), dialkylamide, or the like, if required in the presence of an inert solvent (e.g., halohydrocarbon, ether solvents).

The preferable alkali metal borohydride is lithium, sodium, or potassium borohydride.

In a preferable mode of this invention, 7-amido-3-oxocepham-4-carboxylic acid aralkyl ester or its enolate is dissolved in a dry solvent (preferably N,N-dialkylalkanamide or a mixture of halohydrocarbon and lower alkanol) (3 to 30 volumes per weight) cooled to temperature lower than −20° C. (preferably between −80° C. and −30° C., especially −75° to −40° C.) and mixed with alkali metal borohydride {1 to 20 equivalents (especially 1 to 5 equivalents)} and let react for 10 minutes to 20 hours (especially 30 minutes to 10 hours) to give the desired 7-amido-3-hydroxycepham-4-carboxylic acid aralkyl ester. The product can be used in the reaction of III. Use (1) or (2) below as a starting material.

If required, adding a reaction promoter (e.g., acetic acid) or inert gas (e.g., nitrogen), stirring, or the like usual method for smoothifying a reaction can be applied.

7-AMIDE CLEAVAGE

In the second aspect of this invention, a product of III. Use (2) below (i.e., 7-amido-3-acyloxycepham-4-carboxylic acid aralkyl ester) is subjected to a new amide cleavage [i.e., that consisting of (1) with a mixture of phosphorus pentachloride (1 to 3 equivalents) and aromatic base (e.g., pyridine, picoline, collidine, lutidine, instead of tertiary amine known in the literatures) (1 to 5 equivalents) to give imino-chloride (e.g., at −40° to 0° C. for 1 to 8 hours) and then (2) with lower alkanol (e.g., methanol, ethanol, propanol, isopropanol, butanol, isobutanol, tertiary butanol, ethylene glycol, propylene glycol, glycerin, trimethylene glycol) for converting the imino-chloride into imino-ether and for subjecting the produced imino-ether to alcoholysis giving the desired novel 7-amino-3-acyloxycepham-4-carboxylic acid aralkyl ester (e.g., at −40° to 10° C. for 1 to 5 hours)]. During this procedure, the reaction mixture shows no apparent peak at around 260 nm in its ultraviolet absorption spectrum due to the 3-cephem-4-carboxylate grouping. When tertiary amine is used (as in known amide cleavages) instead of our aromatic base, the product was always a mixture. The product can be used in the reaction of III. Use (4) below as a starting material.

USE (1) The product of I. Reduction above (i.e., 7-amido-3-hydroxycepham-4-carboxylic acid aralkyl ester) is treated with a dehydrating reagent {e.g., (alkyl or aryl)sulfonyl halide (1 to 3 molar equivalents) and trialkylamine (1 to 10 molar equivalents)} in an organic solvent (5 to 20 volumes per weight) at −60° to 30° C. for 1 to 8 hours to give the corresponding 7-amido-3-cephem-4-carboxylic acid aralkyl ester (i.e., the starting material of III. Use 5) below).

(2) The product of I. Reduction above (i.e, 7-amido-3-hydroxycepham compound) is acylated with an acylating agent at −40° to 10° C. for 1 to 150 hours giving 7-amido-3-acyloxycepham compound (i.e., the starting material of II. Amide cleavage above and III. Use (3) below).

(3) The product of II. Use (2) above or (4) below (i.e., 7-amido-3-acyloxycepham-4-carboxylic acid aralkyl ester) is treated with a base (e.g., trialkylamine) at −10° to 20° C. for 5 to 30 hours to eliminate the acyloxy group in a conventional manner giving 7-amido-3-cephem-4-carboxylic acid aralkyl ester (i.e., the starting material of III. Use (5) below).

(4) The product of II. Amido cleavage above (i.e., 7-amino-3-acyloxycepham compound) is acylated with a reactive derivative of carboxylic acid (e.g., chloride, anhydride) to give 7-amido-3-acyloxycepham compound (i.e, the starting material of II. Amido cleavage and III. Use (3) above).

(5) The product of III. Use (1) or (3) above (i.e., 7-amido-3-cephem-4-carboxylic acid aralkyl ester) is easily deprotected giving the corresponding carboxylic acid {e.g., with Lewis acid and a proton scavenger of Japanese Patent Application (Kokai) Sho-52-106891}, that is a potent antibacterial cephalosporin.

Some of thus produced 3-hydroxycepham-4-carboxylic acid esters are also known as intermediates for preparing 3-unsubstituted cephalosporins.

REACTION CONDITION

Each reaction is carried out usually at −80° to 30° C. (especially −50° to −30° C.) for 10 minutes to 10 hours, unless otherwise specified. These are done in an organic solvent, if required under stirring and/or drying. Other usual variations can also be applied.

The reaction solvent can be a hydrocarbon (e.g., pentane, hexane, octane, benzene, toluene, xylene), halohydrocarbon (e.g., dichloromethane, chloroform, carbon tetrachloride, dichloroethane, trichloroethane, chlorobenzene), ether (e.g., diethyl ether, methyl isobutyl ether, anisole, dioxane, tetrahydrofuran), ester (e.g., ethyl acetate, isobutyl acetate, methyl benzoate), nitrile (e.g., acetonitrile, benzonitrile), amide (e.g., formamide, acetamide, dimethylformamide, dimethylacetamide, hexamethylphosphorotriamide), carboxylic acid (e.g., formic acid, acetic acid, propionic acid), organic base (e.g., diethylamine, triethylamine, pyridine, picoline, collidine, quinoline), alcohol (e.g., methanol, ethanol, propanol, hexanol, octanol, benzyl alcohol), or the like industrial solvent or a mixture thereof where suitable.

The objective products can be obtained from the reaction mixture by removing contaminants (e.g., unreacted starting material, by-products, solvents) by a conventional method (e.g., extraction, evaporation, washing, concentration, precipitation, filtration, drying) and worked up conventionally (e.g., by adsorption, elution, distillation, precipitation, separation, chromatography).

Following Examples illustrate the embodiments of this invention.

Amount of the reagents are given in parts (by weight) or equivalents (molar) per the beta-lactam starting material. In the work up, the solutions can be dried over sodium sulfate and vacuum-concentrated. In the case of the acyloxy elimination, the medium is pre-adjusted to pH 9 by adding triethylamine checking with wet pH test strip.

The abbreviations used in the examples and tables are as follows:
BOC=t-butoxycarbonyl.
Bz=benzyl.
Bu-t=t-butyl.
Cbz=carbobenzoxy.
Me=methyl.
Ph=phenyl.

EXAMPLE 1

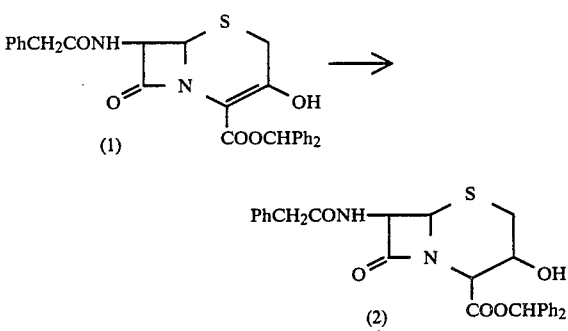

(1) To a solution of 3-oxo-7beta-phenylacetylaminocpham-4-carboxylic acid diphenylmethyl ester (1) or its enolate in a mixture of dichloromethane (6.5 parts) and methanol (4 parts) cooling at −53° C. under nitrogen is added sodium borohydride (4 equivalents) at −57° to −53° C. over 7 minutes. After 30 minutes at the same temperature, glacial acetic acid (1.4 parts) and then water (10 parts) are added gradually to the mixture at the same temperature. The mixture is extracted with dichloromethane. The extract is washed with aqueous 5% aqueous hydrogen carbonate and water, dried over sodium sulfate, and concentrated. The residue is crystallized from a mixture of dichloromethane (4 parts) and n-hexane (1.7 parts) to give 3-hydroxy-7beta-phenylacetylaminocepham-4-carboxylic acid diphenylmethyl ester (2). Yield: 89.7%.

(2) In place of a mixture of methanol and dichloromethane as the reaction solvent of the above reaction, that of ethanol and chloroform (Yield: 78%), that of methanol and dichloromethane (Yield: 81%), or that of methanol, ethanol, and dichloromethane (Yield: 96%) can be used at −80° to −35° C. to give compound (2).

(3) To a solution of 3-hydroxy-7beta-phenylacetylamino-3-cephem-4-carboxylic acid diphenylmethyl ester (1) in dimethylformamide (9.5 parts, dried over Molecular Sieves) at −50° C. under nitrogen is added sodium borohydride (4 equivalents) at −53° to −48° C. over 3 minutes. After 30 minutes at the same temperature, glacial acetic acid (1.4 parts) and then water (10 parts) are added to the mixture gradually, and extracted with ethyl acetate. The extract is washed with 5% aqueous sodium hydrogen carbonate and water, dried over sodium sulfate, and concentrated. The residue is crystallized from a mixture of dichloromethane (4 parts) and n-hexane (1.7 parts) to give 3-hydroxy-7beta-phenylacetylaminocepham-4-carboxylic acid diphenylmethyl ester (2). Yield: 76.3%. mp. 196°–198° C. (decomposition).

IR (Nujol) ν: 3450, 3300, 1765, 1740, 1645 cm$^{-1}$.

NMR (CD$_3$SOCD$_3$) δ: 2.8~3.2 (m, 2H), 3.37 (s, 1H), 3.57 (s, 2H), 4.13 (m, 1H), 4.77 (d, J=6 Hz, 1H), 5.13 (d, J=4.5 Hz, 1H), 5.40 (dd, J$_1$=4.5 Hz, J$_2$=9 Hz, 1H), 6.10 (d, J=9 Hz, 1H), 6.80 (s, 1H), 7.23~7.33 (m, 15H) ppm.

Elemental Analysis: C$_{28}$H$_{26}$N$_2$O$_5$S: Calcd. (%): C, 66.92; H, 5.21; N, 5.57; S, 6.38. Found (%): C, 66.82; H, 5.19; N, 5.70; S, 6.35.

EXAMPLE 2

(Elimination of 3-hydroxy)

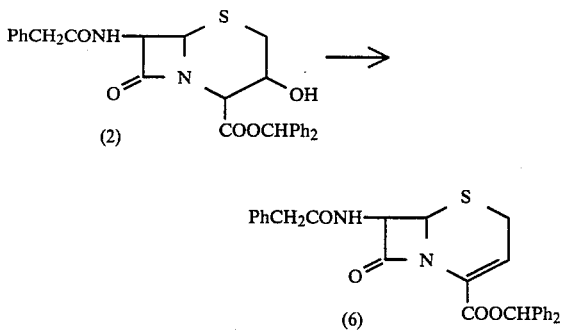

(1) To a suspension of 3-hydroxy-7beta-phenylacetylaminocepham-4-carboxylic acid diphenylmethyl ester (2) in dichloromethane (13 parts) cooling at −10° C. under nitrogen are added triethylamine (4 equivalents) and then methanesulfonyl chloride (2.0 equivalents) at −10° C. over 7 minutes. The produced methanesulfonate ester (3) solution is let react at −10° C. for 30 minutes, and diluted with dichloromethane, washed with water, 5% sulfuric acid, and water, dried over sodium sulfate, and concentrated. The residue is crystallized from methanol (4 parts) to give 7beta-phenylacetylamino-3-cephem-4-carboxylic acid diphenylmethyl ester (6). (Yield: 75.4%).

(2) To a solution of 3-hydroxy-7beta-phenylacetylaminocepham-4-carboxylic acid diphenylmethyl ester (2) in dimethylformamide (9.5 parts, dried over Molecular Sieves) cooling at −50° C. under nitrogen are added triethylamine (4 equivalents) and then methanesulfonyl chloride (2 equivalents) over 3 minutes at −52° to −45° C. After 2.5 hours at −55° to −45° C., the produced methanesulfonate (3) solution is stirred for 50 minutes at −15° to −12° C. diluted with ethyl acetate, washed with water, 5% hydrochloric acid, and water, dried over sodium sulfate, and concentrated. The residue is crystallized from methanol to give 7beta-phenylacetylamino-3-cephem-4-carboxylic acid diphenylmethyl ester (6). (Yield: 81.53%). mp. 166° C. (decomposition).

IR (Nujol) ν: 3250, 1775, 1710, 1645, 1625 cm$^{-1}$.

NMR (CDCl$_3$) δ: 3.30~3.43 (m, 2H), 3.63 (s, 2H), 4.90 (d, J=4.5 Hz, 1H), 5.93 (dd, J$_1$=4.5 Hz, J$_2$=9 Hz, 1H), 6.45~6.67 (m, 2H), 6.90 (s, 1H), 7.30 (m, 15H), ppm.

EXAMPLE 3

(3-O-Acylation)

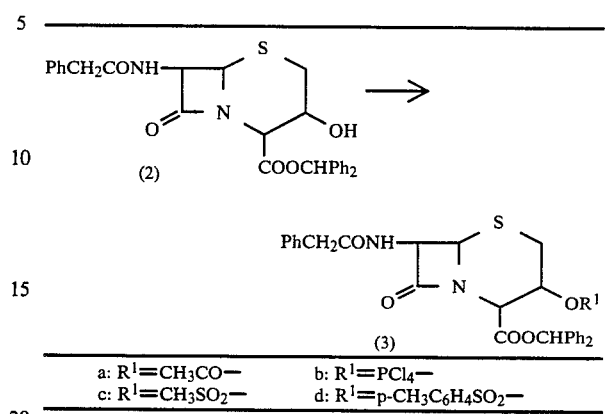

| a: R$^1$=CH$_3$CO— | b: R$^1$=PCl$_4$— |
| c: R$^1$=CH$_3$SO$_2$— | d: R$^1$=p-CH$_3$C$_6$H$_4$SO$_2$— |

A. R$^1$=CH$_3$CO—

To a suspension of 3-hydroxy-7beta-phenylacetylaminocepham-4-carboxylic acid diphenylmethyl ester (2) in dichloromethane (13 parts) at 0° C. are added pyridine (6 equivalents) and acetic anhydride (6 equivalents). After 14 hours at 0° to 5° C., the mixture is diluted with ice-water. The organic layer is taken, washed with hydrochloric acid, aqueous sodium hydrogen carbonate, and water, dried, and concentrated. The reaction is crystallized from a mixture of dichloromethane and hexane to give 3-acetoxy-7beta-phenylacetylaminocepham-4-carboxylic acid diphenylmethyl ester (3a). Yield: 98.1%. mp. 187°–188° C. (decomposition).

IR (Nujol) ν: 3350, 1780, 1740, 1738, 1665 cm$^{-1}$.

NMR (CDCl$_3$) δ: 1.63 (s, 3H), 2.61 (m, 1H), 3.20 (m, 1H), 3.60 (s, 2H), 4.95 (m, 2H), 5.20 (d, J=5 Hz, 1H), 5.55 (dd, J$_1$=5 Hz, J$_2$=9 Hz, 1H), 6.50 (d, J=9 Hz, 1H), 6.83 (s, 1H), 7.27 (m, 15H) ppm.

B. R$^1$=PCl$_4$—

To a suspension of 3-hydroxy-7beta-phenylacetylaminocepham-4-carboxylic acid diphenylmethyl ester (2) in dichloromethane (13 parts) under nitrogen are added pyridine (3 equivalents) at −5° to 0° C. and phosphorus pentachloride (2.7 equivalents) at −25° to −20° C. After 4 hour's stirring at −15° to −10° C., there is obtained a solution of 7-(2-phenyl-2-chloromethylidene)amino-3-tetrachlorophosphonyloxycepham-4-carboxylic acid diphenylmethyl ester (3b).

C. R$^1$=CH$_3$SO$_2$—

To a suspension of 3-hydroxy-7beta-phenylacetylaminocepham-4-carboxylic acid diphenylmethyl ester (2) in dichloromethane (18 parts) cooling at −30° C. are dropwise added methanesulfonyl chloride (6 equivalents) and then pyridine (6 equivalents). The mixture is let stand at 0° to 5° C. for 17 hours. The reaction mixture is diluted with ice-water, the organic layer is taken, washed with hydrochloric acid and water, dried, and concentrated. The residue is crystallized from a mixtue of ethyl acetate and hexane to give 3-methanesulfonyloxy-7beta-phenylacetylaminocepham-4-carboxylic acid diphenylmethyl ester (3c). Yield: 96.5%. mp. 151°–152° C. (decomposition).

IR (Nujol) ν: 3300, 1765, 1720, 1660, 1350, 1180 cm$^{-1}$.

NMR (CDCl$_3$) δ: 2.65 (s, 3H), 2.83 (m, 1H), 3.40 (m, 1H), 3.57 (s, 2H), 4.9~5.1 (m, 2H), 5.20 (d, J=5 Hz,

1H), 5.50 (dd, $J_1=5$ Hz, $J_2=9$ Hz, 1H), 6.43 (d, J=9 Hz, 1H), 6.87 (s, 1H), 7.32 (s, 15H) ppm.

D. $R^1$=p—$CH_3C_6H_4SO_2$—

To a suspension of 3-hydroxy-7beta-phenylacetylaminocepham-4-carboxylic acid diphenylmethyl ester (2) in dichloromethane (9 parts) cooling at 0° C. are added pyridine (6 equivalents) and toluenesulfonyl chloride (6 equivalents). The mixture is let stand at 0° to 5° C. for 105 hours. The reaction mixture is diluted with ice-water, the organic layer is taken, washed with hydrochloric acid and water, dried, and concentrated. The residue is crystallized from a mixture of ethyl acetate and hexane to give 3-p-toluenesulfonyloxy-7beta-phenylacetylaminocepham-4-carboxylic acid diphenylmethyl ester (3d). Yield: 84.7%. mp. 133°-136° C. (decomposition).

IR (Nujol) ν: 3300, 1760, 1730, 1640, 1310, 1180 cm$^{-1}$.

NMR(CDCl$_3$) δ: 2.43 (s, 3H), 2.70 (m, 1H), 3.33 (m, 1H), 3.60 (s, 2H), 4.53~4.90 (m, 2H), 5.20 (d, J=4.5 Hz, 1H), 5.53 (dd, $J_1=4.5$ Hz, $J_2=9$ Hz, 1H), 6.16 (d, J=9 Hz, 1H), 6.83 (s, 1H), 7.32 (m, 17H), 7.63 (d, J=8 Hz, 2H) ppm.

EXAMPLE 4

(7-Amido cleavage)

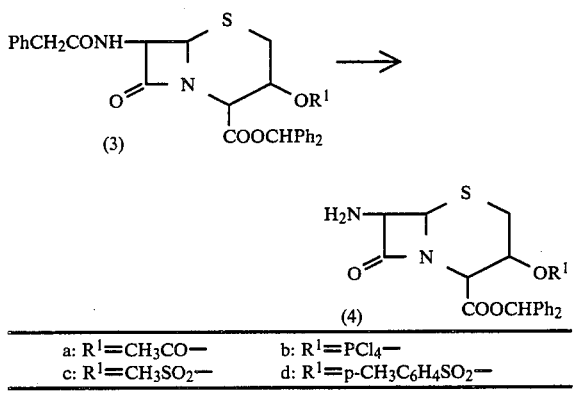

| a: $R^1$=CH$_3$CO— | b: $R^1$=PCl$_4$— |
| c: $R^1$=CH$_3$SO$_2$— | d: $R^1$=p-CH$_3$C$_6$H$_4$SO$_2$— |

A. $R^1$=CH$_3$CO—

To a solution of 3-acetoxy-7beta-phenylacetylaminocepham-4-carboxylic acid diphenylmethyl ester (3a) in dichloromethane (7 parts) cooling at −25° to −20° C. under nitrogen are added pyridine (2 equivalents) and phosphorus pentachloride (1.7 equivalents). After stirring for 4 hours at −15° to −10° C., the mixture is diluted with methanol (12 parts) cooled at −30° C. and stirred at −30° C. for 3.5 hours and at 0° to 5° C. for 2 hours, concentrated, diluted with a mixture of dichloromethane and water, stirred at 0° to 5° for 20 minutes, and the formed organic layer is taken, washed with sodium hydrogen carbonate and water, dried, and concentrated. The residue is dissolved in a small amount of dichloromethane and diluted with ether to separate crystals which is collected by filtration, dissolved in methanol-water, neutralized with aqueous sodium hydrogen carbonate, and diluted with water to crystallize 3-acetoxy-7beta-aminocepham-4-carboxylic acid diphenylmethyl ester (4a). Yield: 80.2%. mp. 155°-156° C. (decomposition).

IR (Nujol) ν: 3350, 3300, 1760, 1750, 1735 cm$^{-1}$.

NMR (CDCl$_3$) δ: 1.60 (s, 3H), 1.77 (m, 2H), 2.70 (m, 1H), 3.27 (m, 1H), 4.40 (m, 1H), 5.13 (m, 3H), 6.90 (s, 1H), 7.23 (s, 10H) ppm.

B. $R^1$=PCl$_4$

The produced solution of Example 3, B. containing 7-(2-phenyl-2-chloromethylidene)amino-3-tetrachlorophosphonyloxycepham-4-carboxylic acid diphenylmethyl ester is added methanol (20 parts) or isobutanol (10 parts) and stirred at 0° to 5° C. for 2 to 3 hours. To the mixture cooled to −25° to −20° C. is dropwise added triethylamine (14 equivalents). After stirring at 0° to 5° C. for 15 hours, the mixture is diluted at −10° to −5° C. with water, stirred for 10 minutes, and extracted with dichloromethane. The extract is washed with hydrochloric acid, water, aqueous 5% sodium hydrogen carbonate, and water, dried, and concentrated. The residue is crystallized from ethyl acetate to give 7-amino-3-cephem-4-carboxylic acid diphenylmethyl ester (5). Yield: 47.3% (in methanol). 37.2% (in isobutanol). mp. 159°-160° C. (decomposition).

C. $R^1$=CH$_3$SO$_2$—

To a solution of 3-methanesulfonyloxy-7beta-phenylacetylaminocepham-4-carboxylic acid diphenylmethyl ester (3c) in dichloromethane (7 parts) cooling at −25° to −20° C. under nitrogen are added pyridine (2 equivalents) and phosphorus pentachloride (1.7 equivalents). After stirring at −15° to −10° C. for 4 hours, the reaction mixture is diluted with methanol (11 parts) cooled at −30° to −25° C. and stirred at −30° C. for 30 minutes and at −5° to 0° C. for 2.5 hours. The reaction mixture is diluted with a mixture of dichloromethane and ice-water and stirred at 0° to 5° C. for 20 minutes. The formed organic layer is taken, washed with water, dried, and concentrated. The residue is dissolved in a small amount of dichloromethane and diluted with ether to separate crystals. The crystals are collected by filtration, dissolved in methanol-water mixture, neutralized with aqueous sodium hydrogen carbonate, and diluted with water to crystallize 3-methanesulfonyloxy-7beta-aminocepham-4-carboxylic acid diphenylmethyl ester (4c). Yield: 55.7%. mp. 145°-147° C. (decomposition).

IR (Nujol) ν: 3350, 3300, 1760, 1735, 1340, 1170 cm$^{-1}$.

NMR (CDCl$_3$) δ: 1.77 (s, 2H), 2.67 (s, 3H), 2.87 (m, 1H), 3.50 (m, 1H), 4.46 (d, J=4 Hz, 1H), 5.13 (m, 2H), 5.20 (d, J=4 Hz, 1H), 6.90 (s, 1H), 7.33 (s, 10H) ppm.

D. $R^1$=p—CH$_3$C$_6$H$_4$SO$_2$—

To a solution of 3-p-toluenesulfonyloxy-7beta-phenylacetylaminocepham-4-carboxylic acid diphenylmethyl ester (3d) in dichloromethane (7 parts) cooling at −25° to −20° C. under nitrogen are added pyridine (2 equivalents) and phosphorus pentachloride (1.7 equivalents). After stirring at −15° to −10° C. for 4 hours, the mixture is diluted with methanol (12 parts) cooled at −30° C., stirred at −30° to −25° C. for 30 minutes and at 0° to 5° C. for 2 hours. The reaction mixture is diluted with dichloromethane and ice-water and stirred at 0° to 5° C. for 20 minutes. The formed organic layer is taken, washed with water, dried, and concentrated. The residue is crystallized from dichloromethane-ether mixture to give 3-p-toluenesulfonyloxy-7beta-aminocepham-4-carboxylic acid diphenylmethyl ester (4d) p-toluenesulfonate salt. mp. 190°-194° C. (decomposition).

IR (Nujol) ν: 1780, 1750, 1360, 1180 cm$^{-1}$.

Elemental Analysis: $C_{34}H_{34}N_2O_9S_3 \cdot H_2O$: Calcd. (%): C, 56.73; H, 4.90; N, 3.89; S, 13.36. Found (%): C, 56.90; H, 4.78; N, 3.97; S, 13.20.

EXAMPLE 5

(Acyloxy Elimination)

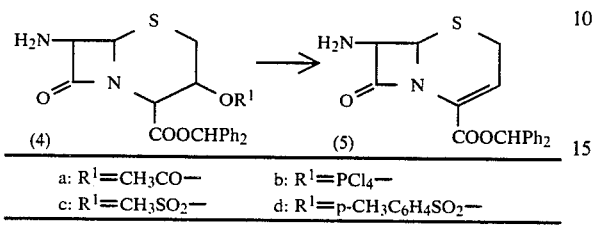

a: $R^1=CH_3CO-$   b: $R^1=PCl_4-$
c: $R^1=CH_3SO_2-$   d: $R^1=p-CH_3C_6H_4SO_2-$

A. $R^1=CH_3CO-$

To a solution of 3-acetoxy-7beta-aminocepham-4-carboxylic acid diphenylmethyl ester (4a) in dichloromethane cooling at −25° to −20° C. is added triethylamine (1 to 3 equivalents). The mixture is warmed slowly up to 0° to 5° C. and let stand overnight. To this is added ice-water (20 parts), stirred for 20 minutes, and extracted with dichloromethane. The extract is washed with hydrochloric acid, water, aqueous 7% sodium hydrogen carbonate, and aqueous 5% sodium chloride, dried, and concentrated. The residue is crystallized from ethyl acetate to give 7beta-amino-3-cephem-4-carboxylic acid diphenylmethyl ester (5). Yield 61.0% from (1). mp. 159°–160° C. (decomposition).

IR (Nujol)$\nu$: 3350, 3300, 1770, 1720, 1630 cm$^{-1}$.

NMR (CDCl$_3$)$\delta$: 2.76(s, 2H), 3.43(m, 2H), 4.83(m, 2H), 6.57(m, 1H), 6.90 (s, 1H), 7.30(s, 10H) ppm.

Similarly, the products of Examples 4A to 4D dissolved in dichloromethane are treated at 0° to 5° C. with triethylamine (1 to 3 equivalents) for 2 to 15 hours to give the same compound.

EXAMPLE 6

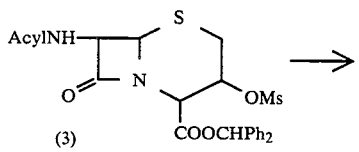

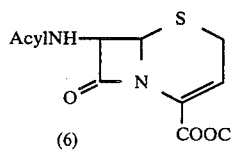

Under a condition similar to that of Example 5, the compounds (6) on Tale 2 are prepared from the corresponding 3-methanesulfonyloxy-7-acylaminocepham-4-carboxylic acid diphenylmethyl ester (3) in dichloromethane by the action of triethylamine (1 to 3 equivalents) at room temperature for 1 to 6 hours.

EXAMPLE 7

(Acylation of 7-amino)

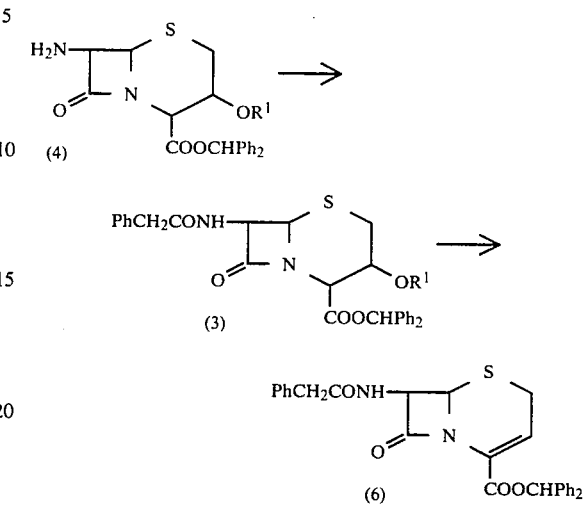

To a solution of 7-amino-3-acetoxycepham-4-carboxylic acid diphenylmethyl ester (4) in dichloromethane (7 parts) cooling at −30° to −10° C. are added pyridine (1.7 equivalents) and phenylacetyl chloride (1.1 equivalents). After stirring for 30 minutes, the mixture is neutralized with triethylamine (1 to 9 equivalents), stirred at 0° to 5° C. for 24 hours, and diluted with ice water. The formed organic layer is taken, washed with hydrochloric acid and water, dried, and concentrated. The residue is crystallized from a mixture of ethyl acetate and ether to give 7beta-phenylacetylamino-3-cephem-4-carboxylic acid diphenylmethyl ester (6). Yield: 70.0%. mp. 170°–171° C. (decomposition).

Under a condition similar to the above, 7-amino-3-acyloxycepham-4-carboxylic acid diphenylmethyl ester (4) in dichloromethane (3 to 10 parts) cooling at −40° to −5° C. are mixed with pyridine (1 to 2 equivalents) and carboxylic acid chloride corresponding to the 7-side chain (1 to 3 equivalents) and stirred for 1 to 24 hours. The reaction mixture is mixed with triethylamine (1 to 3 equivalents), let stand at 0° to 5° C. for 12 hours, washed with hydrochloric acid, water, and aqueous sodium hydrogen carbonate, dried, and concentrated. The residue is crystallized from a mixture of ethyl acetate and ether to give the compounds (6) listed on Table 2.

EXAMPLE 8

(Elimination of 3-acyloxy and 7-acyl)

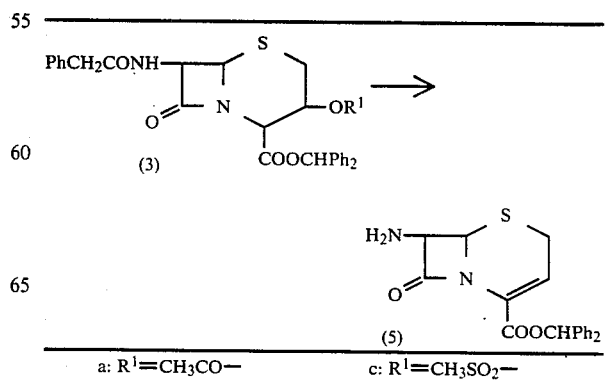

a: $R^1=CH_3CO-$   c: $R^1=CH_3SO_2-$

-continued

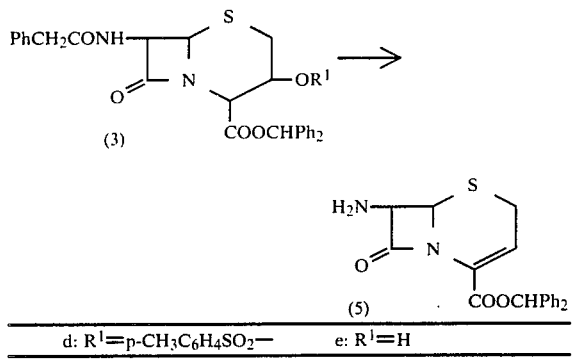

| d: R¹=p-CH₃C₆H₄SO₂— | e: R¹=H |

A. R¹=CH₃CO—

(1) To a solution of 3-acetoxy-7beta-phenylacetylaminocepham-4-carboxylic acid diphenylmethyl ester (3a) in dichloromethane (13 parts) under nitrogen are added at −5° to 0° C. pyridine (2 equivalents) and at −25° to −20° C. phosphorus pentachloride. After stirring at −15° to −10° C. for 4 hours, the mixture is diluted with a mixture of methanol (20 parts) and dichloromethane (5 parts) cooled at −40° to −30° C., and stirred at −30° to −25° C. for 3.5 hours. To the mixture keeping at −25° to −20° C. is dropwise added triethylamine (10.9 equivalents). After keeping at 0° to 5° C. overnight, the mixture is diluted with ice-water (20 parts) and stirred for 20 minutes. The formed organic layer is taken, washed with hydrochloric acid, water, aqueous sodium hydrogen carbonate, and water, dried, and concentrated. The residue is crystallized from ethyl acetate to give 7betaamino-3-cephem-4-carboxylic acid diphenylmethyl ester (5). Yield: 60.2%.

(2) To a solution of the above starting material (3a) in dichloromethane (13 parts) under nitrogen are added at −5° to 0° C. pyridine (2 equivalents) and at −30° to −25° C. phosphorus pentachloride (1.7 equivalents). The mixture is stirred at −15° to −10° C. for 4 hours, cooled to −25° to −30° C., mixed with isobutanol (10 parts) cooled at −30° to −20° C., and let stand at 0° to 5° C. overnight. The reaction mixture is cooled to −20° to −25° C., mixed dropwise with triethylamine (10.9 equivalents), and kept at 0° to 5° C. overnight. The reaction mixture is diluted with dichloromethane (20 parts) and ice water (20 parts) and stirred for 20 minutes. The formed organic layer is taken, washed with hydrochloric acid, water, aqueous sodium hydrogen carbonate, and water, dried, and concentrated. The residue is crystallized from ethyl acetate to give 7beta-amino-3-cephem-4-carboxylic acid diphenylmethyl ester (5). Yield: 60.8%.

C. R¹=CH₃SO₂—

To a solution of 3-methanesulfonyloxy-7beta-phenylacetylaminocepham-4-carboxylic acid diphenylmethyl ester (3c) in dichloromethane (7 parts) cooling at −25° to −20° C. under nitrogen are added pyridine (2 equivalents) and phosphorus pentachloride (1.7 equivalents). After stirring at −15° to −10° C. for 4 hours, the mixture is diluted with methanol (12 parts) cooled at −40° to −30° C. After stirring for 30 minutes at −30° C. and for 2.5 hours at 0° to 5° C., the mixture is cooled to −30° C., mixed dropwise with triethylamine (8.1 equivalents) and let stand overnight at 0° to 5° C. The mixture is diluted with dichloromethane and ice-water and stirred for 20 minutes at 0° to 5° C. The formed organic layer is taken, washed with hydrochloric acid, water, aqueous sodium hydrogen carbonate, and water, dried, and concentrated. The residue is crystallized from ethyl acetate to give 7beta-amino-3-cephem-4-carboxylic acid diphenylmethyl ester (5). Yield: 55.7%.

D. R¹=p—CH₃C₆H₄SO₂—

To a solution of 3-p-toluenesulfonyloxy-7beta-phenylacetylaminocepham-4-carboxylic acid diphenylmethyl ester (3d) in dichloromethane (7 parts) cooling at −15° to −10° C. are added pyridine (2 equivalents) and phosphorus pentachloride (1.7 equivalents). After stirring at −15° to −10° C. for 4 hours, the mixture is diluted with methanol (12 parts) cooled at −40° to −30° C. and then stirred at −30° C. for 30 minutes and at 0° to 5° C. for 2.5 hours. The mixture is cooled to −40° to −30° C., mixed dropwise with triethylamine (8 equivalents), and the mixture is stirred at 0° to 5° C. for 2 hours and let stand overnight. The mixture is diluted with dichloromethane and ice-water and stirred for 20 minutes at 0° to 5° C. The formed organic layer is taken, washed with hydrochloric acid, water, aqueous sodium hydrogen carbonate, and water, dried, and concentrated. The residue is crystallized from ethyl acetate to give 7beta-amino-3-cephem-4-carboxylic acid diphenylmethyl ester (5). Yield: 57.9%.

E. R¹=H (1) To a suspension of 3-hydroxy-7beta-phenylacetylaminocepham-4-carboxylic acid diphenylmethyl ester (3e) in dichloromethane (13 parts) cooling at −5° to 0° C. under nitrogen are added at −5° to 0° C. pyridine (3 equivalents) and at −20° to −25° C. phosphorus pentachloride (2.7 equivalents). After stirring at −15° to −10° C. for 4 hours, the mixture is diluted with methanol (20 parts) cooled at −40° to −30° C. and stirred for 3 hours at −10° to −15° C. The mixture is cooled to −20° to −25° C., mixed dropwise with triethylamine (12 equivalents), and kept at 0° to 5° C. overnight. The mixture is diluted with ice-water (20 parts) and stirred at 0° to 5° C. for 20 minutes. The formed organic layer is washed with hydrochloric acid, water, aqueous sodium hydrogen carbonate, and water, dried, and concentrated. The residue is crystallized from ethyl acetate to give 7beta-amino-3-cephem-4-carboxylic acid diphenylmethyl ester (5). Yield: 47.3%.

(2) To a suspension of the said starting material (3e) in dichloromethane (13 parts) under nitrogen are added at −5° to 0° C. pyridine (3 equivalents) and at −25° to −20° C. phosphorus pentachloride (2.7 equivalents). After stirring at −15° to −10° C. for 4 hours, the mixture is mixed with isobutanol (11 parts) cooled at −40° to −30° C., stirred at 0° to 5° C. for 2 hours, and kept at 0° to 5° C. overnight. The mixture is cooled to −25° to −20° C., mixed dropwise with triethylamine (14 equivalents), and kept at 0° to 5° C. overnight. The mixture is diluted with a mixture of ice-water and dichloromethane, and stirred for 20 minutes. The formed organic layer is taken, washed with hydrochloric acid, water, aqueous sodium hydrogen carbonate, and water, dried, and concentrated. The residue is crystallized from ethyl acetate to give 7beta-amino-3-cephem-4-carboxylic acid diphenylmethyl ester (5). Yield: 37.2%.

PREPARATION

To a solution of 7-amino-3-cephem-4-carboxylic acid diphenylmethyl ester (5) on Table 2 in dichloromethane (7 parts) cooled at 0° C. are added the acid chloride of carboxylic acid corresponding to each 7-side chain (1 to 2 equivalents) and pyridine (1 to 2 equivalents) and stirred for 1 to 5 hours. The reaction mixture is washed with hydrochloric acid and water, dried, and concentrated. The residue is crystallized from a mixture of ethyl acetate and ether to give the corresponding 7-amido-3-cephem-4-carboxy compounds.

TABLE 2

(1) R—NH-β-lactam-S-C(OH)=... COOCHPh$_2$ → (2) R—NH-β-lactam-S-CH(OH)-... COOCHPh$_2$ (3) R—NH-β-lactam-S-CH(OSO$_2$CH$_3$)-... COOCHPh$_2$ → (5) R—NH-β-lactam-S-CH=... COOCHPh$_2$

| R | IR $\nu$(CHCl$_3$): cm$^{-1}$ |
|---|---|
| HNCONH—C(=N-O—)—CH$_2$CO—, CH$_3$ | 3405, 3325, 2975, 1770, 1730, 1705, 1640, 1610. |
| BOCNH—(thiazole)—C(=CH-CH$_3$CH—COOBz)—CO— | 3410, 1778, 1723, 1670, 1280, 1160. |
| (thienyl)—C(=CH~CH$_2$COOBz)—CO— | 3390, 1785, 1725, 1675, 1630, 1495. |
| (thienyl N)—C(=CH~CH$_2$COOBz)—CO— | 1790, 1725, 1680, 1630. |
| CbzNH—(thiazole)—C(=CHCOOBz)—CO— | 3400, 1775, 1725, 1685. |
| CbzNH—(thiazole-N)—C(=CHCH$_2$-COOBz)—CO— | 3200, 1770, 1730, 1690, 1550, 1290. |
| CbzNH—(thiazole)—C(=CH~Cl)—CO— | 3340, 1780, 1720, 1665. |
| CbzNH—(thiazole)—C(=CH—OCH$_2$COOBu-t)—CO— | 3400, 1782, 1730, 1670, 1158, 1130. |
| (thienyl)—CHCO— DL, NHCONH$_2$ | 3500, 3300, 3250, 1790, 1720, 1640 (Nujol). |
| PhCHCO— D, NHBOC | 3400, 1790, 1710, 1695. |
| (thienyl S)—CHCO— D, NHBOC | 3400, 1790, 1720, 1700. |
| CbzNH—(thiazole)—C(=CHCO—NHBOC DL)— | 3400, 1790, 1730, 1700. |
| CbzNH—(thiazole)—C(=C(CO—)—N—NHCOCH$_3$)— | 3180, 1785, 1730, 1655. |
| CONH—CH$_3$ N-O—C(=C-CO—N~OCH$_3$)— | 3410, 3250, 2975, 1790, 1730, 1710, 1640, 1610. |
| CbzNH—(thiazole)—C(=C(CO—)NOCH$_3$)— | 1795, 1735, 1690, 1645. |
| CbzNH—(thiazole)—C(=C(CO—)NOCH$_3$ F)— | 1780, 1730, 1690, 1640. |
| CbzNH—(thiazole)—C(=C(CO—)NOCH$_3$ Cl)— | 3400, 1772, 1723, 1682, 1280, 1038. |
| CbzNH—(thiazole)—C(=CH-CO— OH)— | 3400, 1785, 1730, 1690. |
| CbzNH—(thiazole)—C(=CH-CO— SCH$_2$COOBz)— | 3400, 1795, 1735, 1690. |

What is claimed is:
1. A process for preparing 7-amido-3-hydroxycepham-4-carboxylic acid aralkyl esters which comprises reducing the corresponding 7-amido-3-oxocepham-4-carboxylic acid aralkyl ester or its enolate with an alkali metal borohydride in a dry inert organic solvent at a temperature lower than $-20°$ C.
2. A process as claimed in claim 1, wherein the alkali metal borohydride is lithium, sodium, or potassium borohydride.
3. A process as claimed in claim 1, wherein the inert organic solvent is an anhydrous lower alkanol selected from methanol, ethanol, propanol, butanol, or dialkylamide.
4. A process as claimed in claim 1, wherein the inert organic solvent contains halohydrocarbon or ether as a co-solvent.
5. A process as claimed in claim 1, wherein the reduction is carried out at between $-80°$ C. and $-30°$ C.
6. A process as claimed in claim 1, wherein the reduction is carried out with 1 to 5 equivalents of alkali metal borohydride at between $-75°$ C. and $-40°$ C. over a 30 minutes to 10 hours period.

* * * * *

UNITED STATES PATENT AND TRADEMARK OFFICE
CERTIFICATE OF CORRECTION

PATENT NO. : 4,647,658

DATED : March 3, 1987

INVENTOR(S) : Hamashima et al.

It is certified that error appears in the above-identified patent and that said Letters Patent is hereby corrected as shown below:

1) Column 1, line 6, change "hydroxycephem" to --hydroxycepham--, and

2) Column 1, line 8, change "amido-3-acyloxycephem" to --amido-3-acyloxycepham--.

Signed and Sealed this

Fifth Day of January, 1988

Attest:

DONALD J. QUIGG

Attesting Officer

Commissioner of Patents and Trademarks